(12) United States Patent
Osypka

(10) Patent No.: US 8,588,940 B2
(45) Date of Patent: Nov. 19, 2013

(54) DEVICE FOR THE DEFIBRILLATION OF A HEART

(76) Inventor: Peter Osypka, Rheinfelden-Herten (DE)

( * ) Notice: Subject to any disclaimer, the term of this patent is extended or adjusted under 35 U.S.C. 154(b) by 521 days.

(21) Appl. No.: 12/849,879

(22) Filed: Aug. 4, 2010

(65) Prior Publication Data

US 2011/0034984 A1 Feb. 10, 2011

(30) Foreign Application Priority Data

Aug. 6, 2009 (DE) .......................... 10 2009 036 357

(51) Int. Cl.
*A61N 1/05* (2006.01)
(52) U.S. Cl.
CPC ............. *A61N 1/0563* (2013.01); *A61N 1/0573* (2013.01)
USPC .......................................... 607/122; 607/127
(58) Field of Classification Search
USPC ................. 607/4–5, 116–117, 119, 122–123, 607/125–127; 600/375
See application file for complete search history.

(56) References Cited

U.S. PATENT DOCUMENTS

| 5,433,729 | A | * | 7/1995 | Adams et al. ...................... 607/5 |
| 5,578,067 | A | * | 11/1996 | Ekwall et al. ................. 607/122 |
| 5,824,030 | A | * | 10/1998 | Yang et al. .................... 607/122 |
| 2004/0059402 | A1 | | 3/2004 | Soukup et al. | |

FOREIGN PATENT DOCUMENTS

DE 102008005377 7/2009

\* cited by examiner

*Primary Examiner* — Carl H Layno
*Assistant Examiner* — Jessica Sarcione
(74) *Attorney, Agent, or Firm* — Volpe and Koenig, P.C.

(57) ABSTRACT

In a device (1) for the defibrillation of a heart (2) with an implantable cardiac pacemaker and defibrillator (3), the defibrillation electrode (4) is arranged on the stimulation electrode (5), with the stimulation electrode enclosing the defibrillation electrode. In order to be able to remove the defibrillation electrode without a complicated operation if a defect in the defibrillation electrode (4) occurs during use, it can be moved relative to the stimulation electrode (5) and can be retracted and replaced relative to the implanted stimulation electrode (5) from its position of use, for which the stimulation electrode (5) can be detached or separated from the cardiac pacemaker (3) or its plug (9) provided on this pacemaker.

13 Claims, 4 Drawing Sheets

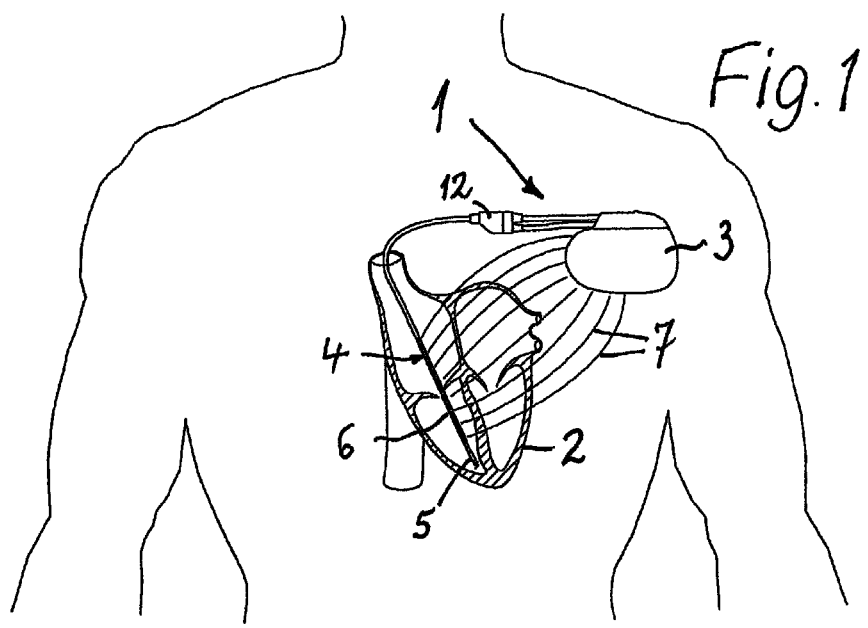
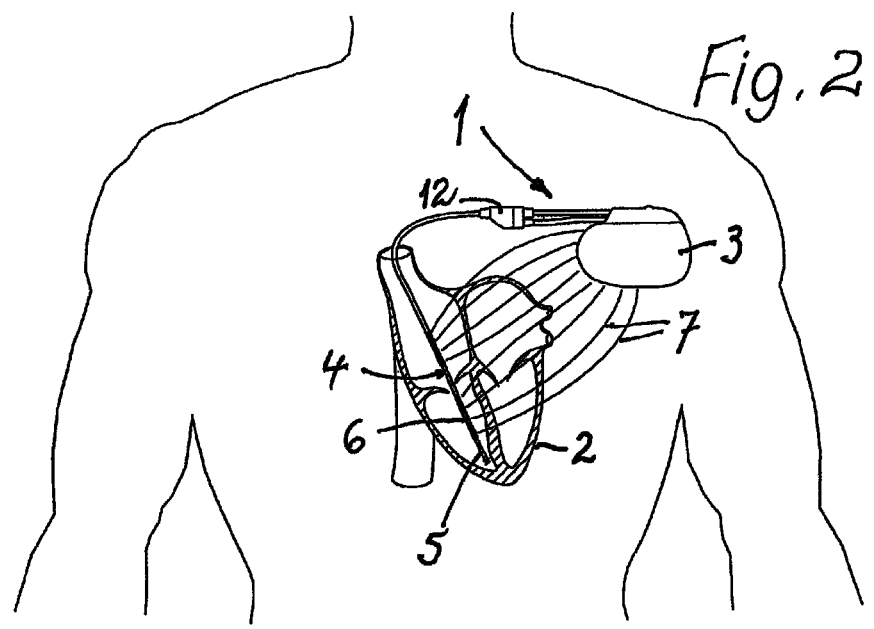

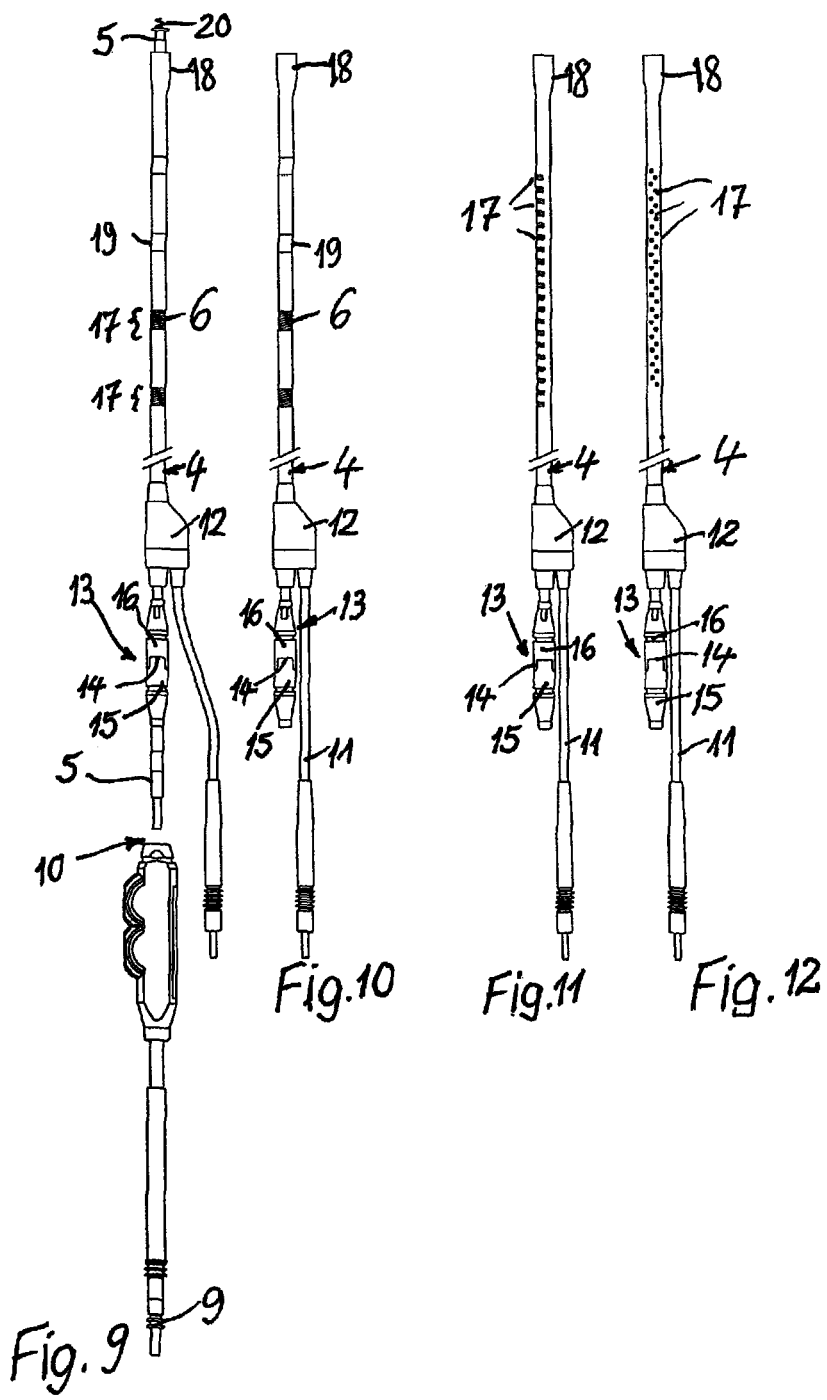

DEVICE FOR THE DEFIBRILLATION OF A HEART

CROSS-REFERENCE TO RELATED APPLICATIONS

This application claims the benefit of German Patent Application No. 10 2009 036 357.2-54, filed Aug. 6, 2009, which is incorporated herein by reference as if fully set forth.

BACKGROUND

The invention relates to a device for the defibrillation of a heart with an implantable cardiac pacemaker and defibrillator, with at least one defibrillation electrode and associated counter electrode, as well as with at least one similarly implantable stimulation electrode, wherein the defibrillation electrode is connected in the position of use to the stimulation electrode, such that the pole of the defibrillation electrode is arranged on the outside of the stimulation electrode.

Such a device is known from practice and is suitable for patients in whom, despite continuously available stimulation, heart chamber fibrillation can occur that must then be immediately counteracted with the defibrillator and the integrated defibrillation electrode.

Because the defibrillation electrode normally has, as a pole, a coil that runs on the outside of the stimulation electrode and because this is often made from platinum, which is a relatively brittle metal that has, indeed, good electrical conductivity but is exposed by the described arrangement to the dynamics of cardiac movements, this can lead to cracks in this defibrillation electrode or its coil, even if this is made from another material, so that its effective length is shortened and is possibly no longer sufficient for defibrillation and the shock required for this.

Indeed, the implanted electrode arrangement could be removed as a whole and replaced by a repaired or new arrangement, but such an operation means too high a risk, in all cases, even for patients who need such a device and electrode arrangement.

SUMMARY

Therefore, the objective arises of creating a device of the type defined above in which the damage produced by a crack in the defibrillation electrode or its pole can be corrected without removing the stimulation electrode.

In order to meet this apparently contradictory objective, the device noted above is provided such that the defibrillation electrode can move relative to the stimulation electrode supporting it and can be retracted and replaced relative to the implanted stimulation electrode from its position of use.

Through this separation according to the invention of the defibrillation electrode from the stimulation electrode with a nevertheless spatial allocation, a possibly defective or broken defibrillation electrode can be removed, so that a tube or similar mount supporting it or its pole can be retracted and provided with a new defibrillation electrode or replaced by a completely new defibrillation electrode with its own tube or its own mount.

Thus, it is preferable and advantageous when the pole of the defibrillation electrode is constructed as an electrically conductive coil that is arranged on a mount that can move relative to the stimulation electrode and can be retracted and replaced with the coil forming the defibrillation electrode or its pole.

Here, the mount for the defibrillation electrode could be, as already mentioned, an inner tube that is arranged so that it can move on the stimulation electrode in the position of use and optionally can be placed detachably. However, it could also be an outer tube that surrounds a possibly broken defibrillation electrode and holds it together for removal.

An advantageous embodiment of the device according to the invention can provide that the stimulation electrode has, in its progression close to the cardiac pacemaker or its plug for this pacemaker, a detachable coupling or separation point or is connected detachably to the cardiac pacemaker and that the mount or the tube is provided with the defibrillation electrode and its connections as a plug part with a branch for the connections, wherein this plug part can be placed on the part of the stimulation electrode leading to the heart and can be moved on this part or pulled away from this part after detachment of the stimulation electrode from the cardiac pacemaker or at the coupling point or at the separation point. Thus, both electrodes could be arranged so that they can move concentrically and relative to each other, but have their own connections for the cardiac pacemaker and defibrillator.

Here it is favorable when the mount having the defibrillation electrode or its pole—in particular, a tube—is constructed so that it can move and be fixed with the branch or a parallel holding device and an attachment point on the stimulation electrode. The branch then has, for example, the corresponding connection or connections for the defibrillator.

The mount or the tube could have, adjacent to the branch, a clamp that is arranged so that it can move in the detached position relative to the stimulation electrode and can be fixed in the clamped position. Thus, with the help of a clamp provided concentric to the stimulation electrode, the relative position of the stimulation electrode and defibrillation electrode can be fixed in the position of use, wherein the clamp can be arranged, in continuation of the defibrillation electrode, parallel to its connection or connections, so that it can move on the stimulation electrode in the open position and can be clamped with this electrode when the entire device has reached its position of use. If the clamp has become detached, it can be pulled out from the stimulation electrode with its connected defibrillation electrode at the separation point of the stimulation electrode. Then, when the repaired or replaced defibrillation electrode has been pushed on and connected to the stimulation electrode at the separation point, the stimulation electrode can also be closed again or connected at its separation point, after which the entire device is functional again.

The clamp for fixing the defibrillation electrode on the stimulation electrode could have a sleeve with an inner hollow space that is continuous in the axial direction for holding the stimulation electrode, wherein the sleeve contain an insert that is elastically deformable in the axial direction against a restoring force or an expandable and/or elastic tube that simultaneously forms or comprises the inner longitudinal hollow space for holding the electrode, wherein the sleeve is divided in the longitudinal direction along a peripheral separation point on its extent into at least two parts that can move relative to each other in the axial direction, wherein the periphery of the separation point is different or profiled or toothed relative to a diameter plane alternately in the axial direction according to opposite sides, so that the front-end, touching edges of the parts of the sleeve are connected with a positive fit in the direction of rotation, wherein furthermore the parts of the sleeve can be pulled apart in the axial direction against the restoring force of the elastic insert or tube holding them together so far that the mutual profiling is detached and can be rotated relative to each other under torque or twisting of the elastic insert or sleeve and can be fixed in the rotated position, in turn, in contact with each other against rotational movements.

Such a clamp can be operated very easily, because the user must move its two parts relative to each other, according to which the axial movement of one of the two parts is also sufficient, after which a relative rotation leads to narrowing of the inner hollow space, so that, after leading the two parts together in their position of use, a clamping effect occurs. The clamp thus corresponds essentially to a clamp thus is already known in another context according to DE 10 2005 016 364 B3 and also has the advantages described therein.

The coil forming the defibrillation pole can be divided in the longitudinal direction into at least two sections whose spacing is selected so that one section is provided for placement in the ventricle and the other section is provided for placement in the atrium of the heart. The defibrillation electrode arranged coaxial to the stimulation electrode is effective accordingly.

One refinement can provide that the spacing of the sections forming the defibrillation pole is variable. This allows adaptation to different anatomical conditions.

Here it can be preferred when, for changing the spacing of the sections forming the defibrillation pole, these are each arranged on mounts or tube parts that are arranged concentric to each other and whose longer mount or whose longer tube part supports the section of the defibrillation electrode arranged in the position of use in the ventricle and that the other section of the coil of the defibrillation electrode that can move or be displaced relative to the first section is arranged on a shorter mount or a tube part arranged on the outside of the first mount or the tube part. In this way, the optimal setting for defibrillation is possible for the spacing of the two sections and poles for adaptation to the corresponding anatomy of a heart.

Here it is advantageous when the two tube parts are connected in the position of use rigidly or by a clamp and can be moved or retracted together relative to the stimulation electrode when replacing the defibrillation electrode. Furthermore, the sections can be connected to each other by another clamp that is detachable for a relative movement of the two sections.

However, it is also conceivable that a single clamp is provided for attaching the defibrillation electrode as a whole on the stimulation electrode with which the two sections of the defibrillation electrode are simultaneously fixed on each other in the position of use.

One construction of the invention, especially for reducing the required energy for the defibrillation, can provide that the pole region of the defibrillation electrode, especially the coil of the defibrillation electrode forming the pole or poles—optionally on its two sections—is covered with an insulating or silicone tube having individual openings or windows. The current can flow at the openings, but it is then limited to these openings or windows, so that correspondingly less current must be discharged. Simultaneously, the coil of the defibrillation electrode is protected against the in-growth of connective tissue.

The openings or windows of the insulating tube could be slots or perforations or at least one break running across at least one part of the periphery of the insulating tube.

Another construction for increasing the effectiveness can provide that, in the region of an opening, a window, or a break in the insulation tube, at least one platinum sleeve is arranged on the coil forming the defibrillation electrode and its pole. This has very good conductivity and is simultaneously biocompatible with the surrounding tissue.

The device according to the invention can be constructed such that the defibrillation electrode and the stimulation electrode held or enclosed by it are implantable in the assembled position, wherein the defibrillation electrode can be pushed relative to the stimulation electrode due to its ability for relative, axial displacement relative to the stimulation electrode so far that it holds and encloses the distal anchoring end or a screw coil of the stimulation electrode forming this end—with which this is fixed in the position of use in the heart tissue—and that, at the end of the insertion process, the defibrillation electrode can be retracted and adjusted and/or fixed relative to the stimulation electrode in its position of use. This fixing can be performed, for example, with the already described and explained clamp.

The ability for displacement of the defibrillation electrode is thus used to improve and to simplify the implantation, especially when the stimulation electrode advantageously has, on its distal end, a screw coil for its fixing that could, without such protection by the defibrillation electrode, come in contact with and damage the inner vessel wall during the implantation process, if it is constructed so that it cannot be retracted on its side relative to the stimulation electrode. The stimulation electrode with the screw coil can thus have a correspondingly simple construction without a mechanism for adjusting the screw coil, because the screw coil could be enclosed during the implantation by the movable defibrillation electrode according to the invention.

Above all, for the combination of individual or several of the features and measures described above, a device having of a stimulation electrode and a defibrillation electrode is produced in which the defibrillation electrode can move relative to the stimulation electrode and thus can be pulled away due to a possible separation of the stimulation electrode from the cardiac pacemaker or in its progression completely from the stimulation electrode, in order to exchange it for a new defibrillation electrode. Preferably, the stimulation electrode is here constructed in the region of its connection to the cardiac pacemaker so that it is detachable from the pacemaker so that a free end of this stimulation electrode is formed after the detachment, wherein the cross section of this free end allows the defibrillation electrode having a continuous lumen to be placed and pushed onto the stimulation electrode. The separation point of the stimulation electrode is thus preferably constructed so that its plug is detached from the defibrillation electrode during placement or detachment of this defibrillation electrode.

BRIEF DESCRIPTION OF THE DRAWINGS

Below, embodiments of the invention will be described with reference to the drawing. Shown in partially schematic diagram are:

FIG. 1 is a view of an implanted device according to the invention for defibrillation with a combination cardiac pacemaker and defibrillator arranged in the position of use, wherein the defibrillation electrode is arranged concentrically on the outside on the stimulation electrode and its connection is provided so that it can move on a branch parallel to the connection of the stimulation electrode, wherein the single pole of the defibrillator electrode constructed as a coil is so long that it is effective simultaneously in the atrium and in the ventricle, FIG. 2 is a view corresponding to FIG. 1, wherein the pole of the defibrillation electrode is divided and the two sections have a spacing such that one section is arranged in the atrium and the other section is arranged in the ventricle, FIG. 9 is a view of an embodiment in which the defibrillation electrode is covered by an insulating tube that has openings for its poles, FIG. 10 is a view of the defibrillation electrode according to FIG. 9 after the detachment from the stimulation electrode or before its placement thereon, and FIG. 11 and FIG. 12 are views of modified embodiments of defibrillation electrodes whose poles are covered with an insulating tube that has different openings or perforations.

DETAILED DESCRIPTION OF THE PREFERRED EMBODIMENTS

Figure 3:
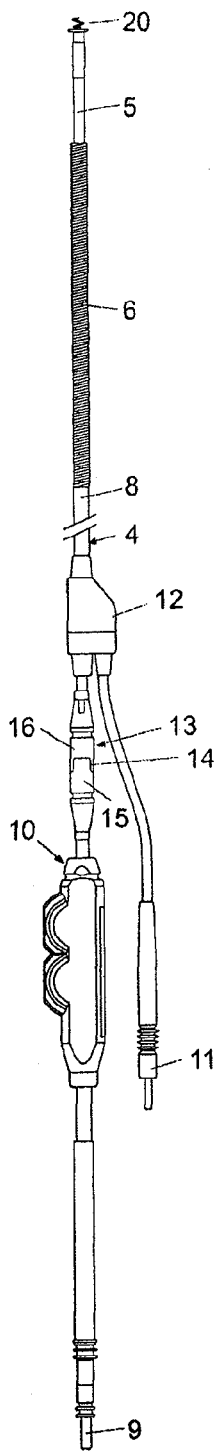
FIG. 3 is an enlarged scale view of the stimulation electrode and the defibrillation electrode arranged according to the invention concentric to the stimulation electrode and has a mount and a branch for its connection, wherein the mount is passed through by the stimulation electrode and the stimulation electrode has a coupling for its connection to the cardiac pacemaker, wherein a clamp is provided between this connection and the branch, with which the stimulation electrode can be fixed on the part of the stimulation electrode leading through the branch.

In the following description of different embodiments, parts that are matching with respect to their function are also given matching reference symbols even if they have different constructions.

A device designated as a whole with 1 is used for the defibrillation of a heart 2 and comprises an implantable, combination cardiac pacemaker and defibrillator 3, also called below only "cardiac pacemaker 3" or "defibrillator 3," a defibrillation electrode 4 with associated counter electrode that is formed by the cardiac-pacemaker housing, as well as a similarly implantable stimulation electrode 5 that is shown in FIGS. 1 and 2 in the position of use and that is simultaneously effective as the sensing electrode.

According to FIGS. 1, 2, 3, 4, 6, 7, and 9, the defibrillation electrode 4 is connected in the position of use to the stimulation electrode 5 in a way still to be described, such that the pole 6 of the defibrillation electrode 4 is arranged on the outside of the stimulation electrode 5.

In this way, a very effective defibrillation can be performed with a favorable field-intensity distribution that is indicated by field lines 7 in FIGS. 1 and 2.

In all of the embodiments it is provided that the defibrillation electrode 4 can be retracted relative to the stimulation electrode 5 surrounding the defibrillation electrode, and can be shifted and moved relative to the implanted stimulation electrode 5 from its position of use and replaced in a way still to be explained. Thus it is possible, in the case of defective functions of the defibrillation electrode 4 that can occur, for example, due to a break, to be able to remove this electrode without a complicated operation, because the stimulation electrode 5 can remain implanted. With a relatively small operation it is possible to pull the defibrillation electrode 4 away from the stimulation electrode 5 and to replace it by a new defibrillation electrode 4.

In the embodiments, the already mentioned pole 6 of the defibrillation electrode 4 is constructed as an electrically conductive coil, which is indicated in the drawings. This coil forming the pole 6 is here arranged in a way that is not shown in more detail on a mount that can move relative to the stimulation electrode 5 and is preferably a tube 8 and can be retracted and exchanged with the defibrillation electrode 4 or coil forming its pole. The tube 8 used as the mount is thus movable in the position of use on the stimulation electrode 5 and is arranged so that it can be fixed in a way still to be described.

Figure 4:
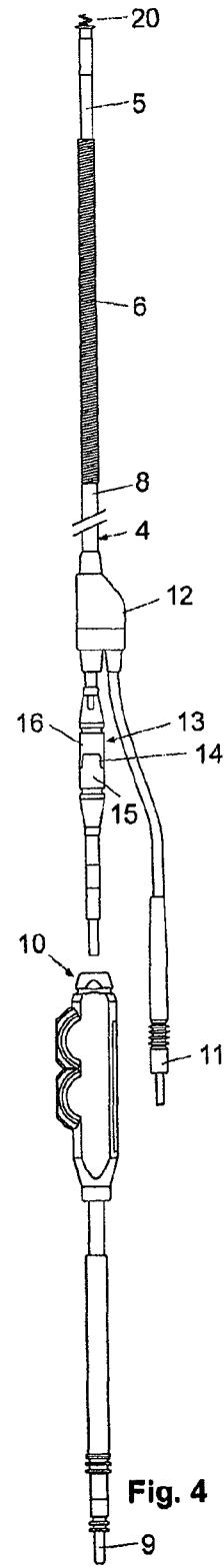
FIG. 4 is a view of the arrangement according to FIG. 3 after the detachment of the separation point of the stimulation electrode, wherein the stimulation electrode can be pulled back and placed again over the free end of the stimulation electrode in the region of the separation.
Figure 6:
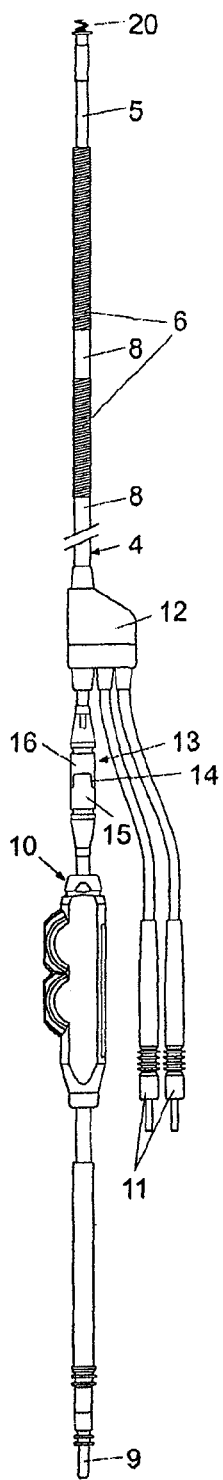
FIG. 6 is a view of a modified embodiment in which the pole of the defibrillation electrode is divided and for each section in the region of the branch a separate connection is provided according to the embodiment according to FIG. 2.
Figure 7:
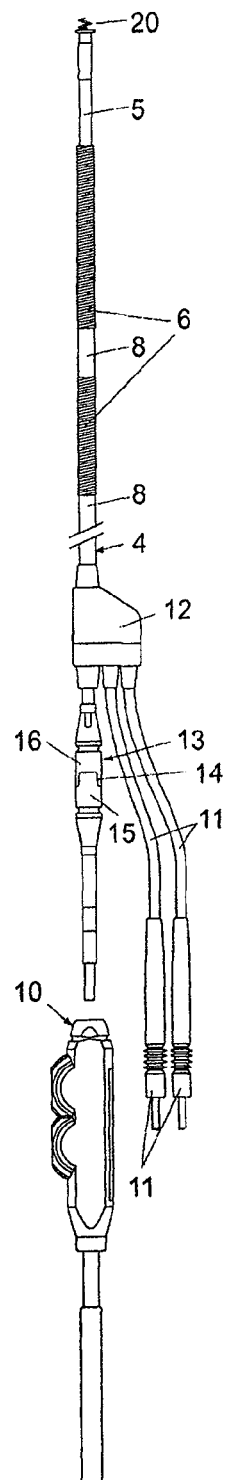
FIG. 7 is a view showing the separation of the stimulation electrode from its connection, wherein the defibrillation electrode provided with two poles is still placed on the stimulation electrode.

In the comparison of FIGS. 3 and 4 or 6 and 7, as well as with reference to FIG. 9, one sees that the stimulation electrode 5 has, in its progression close to the cardiac pacemaker 3, on the side facing away from the cardiac pacemaker 3 for its plug 9 that can be inserted therein, a detachable coupling or separation point 10 that is closed or connected in FIGS. 3 and 6 and is opened or separated in FIGS. 4 and 7.

In these and in other figures, one further sees that the mount or the tube 8 with the defibrillation electrode 4 and its connection or connections 11 for the defibrillator 3 as a plug part is provided with a branch 12 for these connections 11. The connection or connections 11 are thus connected electrically within this branch 12 to the pole or poles 6 of the defibrillation electrode 4.

This plug part made from tube 8 and branch 12 can be placed and pushed onto the part of the stimulation electrode 5 leading to the heart 2 after detachment of the stimulation electrode 5 from the cardiac pacemaker 3 or at the separation point 10 or, in the case of an exchange, this plug part can be pulled away from the stimulation electrode 5 past its separated end.

Instead of a coupling with separation point 10, the plug 9 could also be connected detachably directly to the stimulation electrode 5, in order to allow the placement or pulling of the defibrillation electrode without colliding with the plug 9.

The mount, that is, the tube 8, with the defibrillation electrode 4 or its pole 6 is constructed so that it can be moved and fixed with the branch 12 and an attachment point still to be described at the stimulation electrode 5. For this purpose, in the embodiment it is provided that the mount or the tube 8 has, adjacent to the branch 12 on its distal side, a clamp 13 that is passed through by the stimulation electrode 5 in the position of use and is movable in the detached position relative to the stimulation electrode 5 and is fixed in the clamped position.

Figure 5:
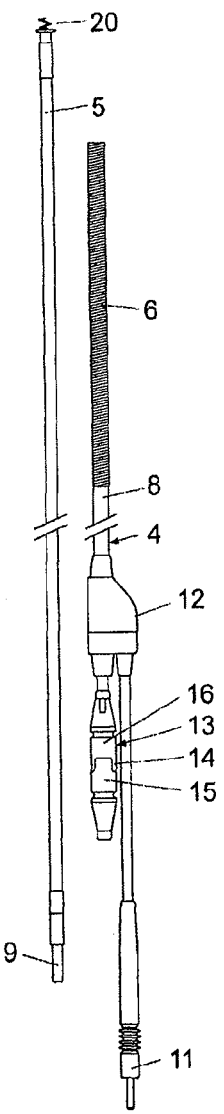
FIG. 5 is a view of the free stimulation electrode and the stimulation electrode separated from it, pulled back from it, or placed on it with the clamp located on it.
Figure 8:
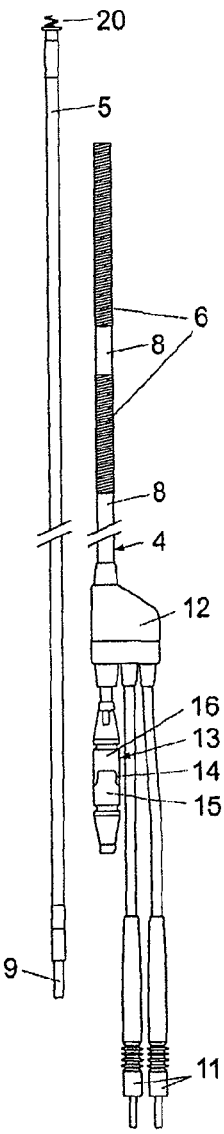
FIG. 8 is a view according to FIG. 7 and analogous to FIG. 5 after pulling away or before placing the defibrillation electrode on the stimulation electrode.

After separation of the stimulation electrode 4 in the region of its separation point 10, the defibrillation electrode 4 with its branch 12 and the clamp 13 can thus be pushed onto the stimulation electrode 5, as, in the reverse, after such separation, the defibrillation electrode 4 can be pulled with its branch 12 and its clamp 13 from the stimulation electrode 5. FIGS. 5 and 8 each show, one next to the other, the correspondingly narrow stimulation electrode 5 after its separation point 10, wherein the defibrillation electrode 4 shown next to it can be pushed with its branch 12 and the clamp 13 onto this stimulation electrode. In the same way, these figures are the representation after a corresponding separation of the two electrodes.

The clamp 13 is constructed in the embodiment like a clamp described for a different application purpose in DE 10 2005 016 364 B3. For fixing the defibrillation electrode 4 on the stimulation electrode 5, it has a sleeve not shown in detail in the mentioned patent specification with an inner hollow space passing through in the axial direction for holding the stimulation electrode 5, wherein this sleeve of the clamp 13 contains an insert that is elastically deformable in the axial direction against a restoring force or an expandable and/or elastic tube that simultaneously forms and comprises the inner longitudinal hollow space for holding the stimulation electrode 5. The sleeve is divided in the longitudinal direction along a peripheral separation point 14 on its extent into two parts 15 and 16 that can move relative to each other in the axial direction, wherein the periphery of the separation point 14 is different opposite a diameter plane running perpendicular to the plane of the drawing alternately in the axial direction according to opposite sides, that is, has a profiling that is different from ring-shaped contours or is toothed, so that the front-end, touching edges of the parts 15 and 16 are connected with a positive fit in the rotational direction. As explained in DE 10 2005 016 364 B3, the parts 15 and 16 can be pulled apart in the axial direction against the restoring force of the elastic insert or tube holding them together so far that the mutual profiling is detached and the two parts 15 and 16 can be rotated relative to each other under torque or twisting and thus narrowing of the elastic insert or tube and can be brought into contact with each other, in turn, in the rotated position and can be fixed against rotational movements and can be connected with a non-positive fit with the stimulation electrode. For example, the part 15 can be retracted relative to the part 16 from this part and from the branch 12, rotated partially or multiple times, and brought back into the position of use, after which the defibrillation electrode 4 with the branch 12 and the clamp 13 was placed on a stimulation electrode 5 that is therefore clamped rigidly.

While in the embodiments according to FIGS. 1 and 3 to 5 the coil forming the defibrillation pole 6 is continuous and can be effective according to FIG. 1 both in the atrium and also in the ventricle of the heart 2, in the embodiments according to FIGS. 2, 6 to 8, 9, and 10, it is provided that this coil forming the defibrillation pole 6 is divided in the longitudinal direction into at least two sections whose spacing according to FIG. 2 is selected so that one section is provided and suitable for placement in the ventricle and the other section is provided and suitable for placement in the atrium of the heart 2. Here, for each of these sections on the branch 12, a corresponding connection 11 is provided. Thus, it is possible to load each of these sections with a defibrillation current.

Furthermore, this spacing of the sections forming the defibrillation pole 6 can be variable, wherein, for such a change of the sections forming the defibrillation pole or poles 6, each section can be arranged on mounts or tube parts arranged concentric to each other, whose longer mount or whose longer tube part supports the section of the defibrillation electrode 4 that is arranged in the ventricle in the position of use. The other section of the coil of the defibrillation electrode 4 provided for the atrium and adjustable or movable relative to this first section can then be formed on a shorter mount or tube part arranged on the outside of the first mount or tube part, so that this can be moved relative to the inner tube part.

In the position of use, the two tube parts can be connected rigidly or by a clamp, for example, also the clamp 13, and can be moved or retracted for replacement of the defibrillation electrode 4 together relative to the stimulation electrode 5.

In FIGS. 9 to 12, modified embodiments are shown in which the pole region of the defibrillation electrode 4 and here the coil forming the pole or poles 6 is covered with an insulating or silicone tube 18 having individual openings 17 or windows.

FIGS. 11 and 12 show embodiments in which the openings 17 or windows of the insulating tube 18 are slots (FIG. 11) or perforations (FIG. 12). In FIGS. 9 and 10, it is shown that the openings 17 can be breaks running on the periphery of the insulating tube 18, wherein these breaks preferably do not run across the entire extent, so that they can also transmit forces in the pulling direction.

In FIGS. 9 and 10 it is also indicated that, in the region of an opening 17 or a window or a break of the insulating tube 18, at least one platinum sleeve 19 could be arranged on the defibrillation electrode as pole 6, in order to improve the stimulation transmission.

For the devices 1 shown in FIG. 1 or 2, the defibrillation electrode 4 and the stimulation electrode 5 held concentrically by this in the interior is implantable in the assembled position. Here, the defibrillation electrode 4 is first pushed relative to the stimulation electrode 5 in a way that is not shown in detail so far past its distal end that it holds and encloses the anchoring end and a screw coil 20 of the stimulation electrode 5 forming this end. If one considers, for example, FIG. 9, it can be easily seen that relative to the position of use shown there, the defibrillation electrode 4 can and will be pushed so far that the screw coil 20 is enclosed at the distal end of the stimulation electrode 5 by the defibrillation electrode 4. At the end of such an implantation process, the defibrillation electrode 4 can then be retracted relative to the stimulation electrode 5 into its position of use according to FIG. 3, 6, or 9, adjusted, and/or fixed, in particular, with the help of the clamp 13. Thus, the defibrillation electrode 4 that can move relative to the stimulation electrode 5 obtains an additional function for the first implantation of the entire device 1 in that it encloses the screw coil 20, so that this cannot lead to injuries on the inside of a vessel.

For the device 1 for the defibrillation of a heart 2 with an implantable cardiac pacemaker and defibrillator 3, the defibrillation electrode 4 is arranged on the stimulation electrode 5 and surrounding this electrode. In order to be able to remove this defibrillation electrode without a complicated operation in the case of a defect occurring in the defibrillation electrode 4 during use, it can be moved relative to the stimulation electrode 5 and can be retracted and exchanged relative to the implanted stimulation electrode 5 from its position of use, for which the stimulation electrode 5 can be detached or separated from the cardiac pacemaker 3 or its plug 9 provided on this pacemaker.

The invention claimed is:

1. Device (1) for defibrillation of a heart (2) comprising an implantable cardiac pacemaker and defibrillator (3), at least one defibrillation electrode (4) and associated counter electrode, at least one implantable stimulation electrode (5), the defibrillation electrode (4) is connected in a position of use to the stimulation electrode (5) such that a pole (6) of the defibrillation electrode (4) is arranged on an outside of the stimulation electrode (5), and the defibrillation electrode is moveable relative to the stimulation electrode (5) and is retractable from the position of use and is adapted to be exchangeable relative to the stimulation electrode (5) that remains implanted in the position of use, wherein the pole (6) of the defibrillation electrode (4) is constructed as an electrically conductive coil arranged on a mount that is moveable relative to the stimulation electrode (5), with which the coil forming the defibrillation electrode (4) or the pole (6) is adapted to be retracted and exchanged, and the mount for the defibrillation electrode is an inner tube (8) that is arranged so that it is moveable on the stimulation electrode (5) in the position of use.

2. The device according to claim 1, wherein the stimulation electrode (5) has in its progression in a region adapted to be close to the cardiac pacemaker (3) or a plug (9) of the cardiac pacemaker a detachable coupling or separation point (10) or is connected detachably to the cardiac pacemaker (3) and the mount or the tube (8) is provided with the defibrillation electrode (4) and a connection or connections (11) as a plug part with a branch (12) for the connection or connections (11), wherein the plug part is adapted to be placed on the part of the stimulation electrode (5) leading to the heart (2) after detaching the stimulation electrode (5) from the cardiac pacemaker (3) or at the separation point (10) and can be moved on the electrode or pulled away from the electrode.

3. The device according to claim 2, wherein the mount having the defibrillation electrode (4) or the pole (6) is constructed so that it is adapted to be moved and fixed in place with the branch (12) or parallel holding device and an attachment point on the stimulation electrode (5).

4. The device according to claim 1, wherein the mount or the tube (8) has, adjacent to the branch (12), a clamp (13) that is adapted to be moved in a detached position relative to the stimulation electrode (5) and is fixed on the electrode in a clamped position.

5. The device according to claim 4, wherein the clamp (13) has, for fixing the defibrillation electrode (4) on the stimulation electrode (5), a sleeve with an inner hollow space continuous in an axial direction for holding the stimulation electrode (5), the sleeve contains an insert that is elastically deformable in the axial direction against a restoring force or at least one of an expandable or elastic tube that simultaneously forms or comprises an inner longitudinal hollow space for holding the stimulation electrode (5), and the sleeve is divided in a longitudinal direction along a separation point (14) peripheral on its extent into at least two parts (15, 16) that can move relative to each other in the axial direction, the separation point (14) has a periphery that is different in the axial direction according to opposite sides alternately relative to a diameter plane or is profiled or toothed, so that a frontend, touching edges of the at least two parts (15, 16) of the sleeve are connected with a positive fit in a rotational direction, and the at least two parts (15, 16) can be pulled apart in the axial direction against the restoring force of the elastic insert or tube holding the at least two parts together so that a mutual profiling is detached and the at least two parts (15, 16) are rotated relative to each other while torque or twisting the elastic insert or tube and can be fixed in contact with each other against rotational movements, in turn, in a rotated position.

6. The device according to claim 5, wherein a coil forming the defibrillation pole (6) is divided in the longitudinal direction into at least two sections whose spacing is selected so that one section is adapted for placement in a ventricle and the other section is adapted for placement in an atrium of the heart (2).

7. The device according to claim 6, wherein a spacing of the sections forming the defibrillation pole (6) is variable.

8. The device according to claim 7, wherein for changing the spacing of the sections forming the defibrillation pole (6), the sections are each arranged on the mounts or tube parts that are arranged concentrically relative to each other and a longer one of the mounts or a longer one of the tube parts carries the section of the defibrillation electrode (4) that is adapted to be arranged in the position of use in the ventricle and the other section of the coil of the defibrillation electrode (4) that can be moved or displaced relative to the first section is placed on a shorter one of the mounts or tube part arranged on an outside of the first mount or the tube part.

9. The device according to claim 8, wherein the two tube parts are connected in the position of use rigidly or by the clamp (13) and are adapted to be displaced or retracted together relative to the stimulation electrode (5) during an exchange of the defibrillation electrode.

10. The device according to claim 9, wherein a pole region of the defibrillation electrode (4) defined by the coil forming the pole or poles (6) is covered with an insulating or silicone tube (18) having individual openings (17) or windows.

11. The device according to claim 10, wherein the openings (17) or windows of the insulating tube (18) are slots or perforations or at least one break running across at least one part of the extent of the insulating tube (18).

12. The device according to claim 11, wherein in a region of one of the openings, windows, or breaks of the insulating tube (18), at least one platinum sleeve (19) is arranged on the coil forming the defibrillation electrode.

13. The device according to claim 1, wherein the defibrillation electrode (4) and the stimulation electrode (5) are adapted to be held in an assembled position, and the defibrillation electrode (4) is adapted to be shifted relative to the stimulation electrode (5) so far that it holds and encloses an anchoring end or a screw coil (20) of the stimulation electrode (5) forming the end, and at an end of an implantation process, the defibrillation electrode (4) is adapted to be retracted and at least one of adjusted or fixed in its position of use relative to the stimulation electrode (5).

\* \* \* \* \*